United States Patent [19]

Bick

[11] 4,057,628

[45] Nov. 8, 1977

[54] REMOVAL OF HEPATITIS ASSOCIATED ANTIGEN FROM PLASMA

[75] Inventor: Rodger L. Bick, Los Angeles, Calif.

[73] Assignees: William L. Wilson; Rodger L. Bick; Lajos F. Fekete, all of Santa Monica, Calif.

[21] Appl. No.: 678,024

[22] Filed: Apr. 19, 1976

[51] Int. Cl.$^2$ ............... A61K 35/16; A61K 39/12; C12K 7/00

[52] U.S. Cl. ............... 424/101; 195/1.5; 424/89

[58] Field of Search ............ 424/89, 101; 195/1.5

[56] References Cited

U.S. PATENT DOCUMENTS

| | | | |
|---|---|---|---|
| 3,880,989 | 4/1975 | Garcia | 424/85 |
| 3,893,990 | 7/1975 | Fekete | 260/112 B |
| 3,956,259 | 5/1976 | Garcia | 260/112 B |

*Primary Examiner*—Sam Rosen

[57] ABSTRACT

Hepatitis associated antigen is removed from plasma and plasma fractions by admixing the plasma with ethylene oxide-propylene glycol condensation product at a temperature of from about 0° to 39° centigrade. Under these conditions a precipitate is formed. The concentration of condensation product is adjusted so that all of the hepatitis associated antigen remains either in the precipitate or the liquid phase. Separation of the resultant liquid and solid phases produces a liquid phase which is entirely free of the undesired antigen. The concentration of condensation product which is required to cause complete precipitation of hepatitis associated antigen increases with increasing temperature from a value of about 9 percent, on a weight per volume basis, at about 0° centigrades to a value of about 28 percent at about 39° centigrade. All of the hepatitis associated antigen remains in the liquid phase at condensation product concentrations of less than about 7 percent at about 9° centigrade and about 15 percent at about 39° centigrade. At intermediate concentrations hepatitis associated antigen appears in both phases.

4 Claims, No Drawings

REMOVAL OF HEPATITIS ASSOCIATED ANTIGEN FROM PLASMA

This invention relates to the production of plasma and plasma fractions which are free from hepatitis associated antigen.

Many patients require blood transfusions for one reason or another. Hepatitis is a relatively common disease which is transmitted from donor to receipient through the transfusion of blood. Previously there was considerable difficulty in avoiding the transmission of hepatitis from donor to recipient. According to the present invention, this problem is solved by removing the undesired hepatitis associated antigen from the blood plasma fractions before they are administered to the recipient.

Whole blood is removed from the donor and is centrifuged to separate out the red blood cells. The remaining plasma is, according to conventional procedures, pooled, treated to concentrate it and to separate it into various plasma fractions. In general conventional commercial concentration procedures result in concentrating approximately 6,000 liters of plasma down to about 10 liters of concentrate. The various fractions which result from the concentration and separation procedures are lyophilized so as to produce dry products. The dry products are shipped and stored at the site of use. When their use is required, the lyophilized products are solubilized by dissolving them in sterile water or saline solution.

Plasma from many different donors is combined or pooled to produce one large batch of plasma for purposes of concentration. If one donor has hepatitis, then the entire batch of pooled plasma is contaminated. Since approximately 30 percent of the population gives a positive reaction when tested for hepatitis, most concentrated plasma contains hepatitis associated antigen. Certain blood plasma fractions such as albumin may be treated with heat to kill the undesired hepatitis associated antigen. Heat, unfortunately, will destroy some blood fractions so that heating procedures are not available for the treatment of these fractions. Chromatographic techniques may be utilized on small quantities of blood plasma to separate out the undesired hepatitis associated antigen, but this technique is not practical for large volumes of blood plasma. Most of the coagulation protein fractions cannot be treated with heat to remove the hepatitis associated antigen. These fractions are used in large quantities in the treatment of hemophiliacs. Hemophiliac patients very often contract hepatitis because of the large quantities of coagulation protein fractions that they receive during treatment.

According to the present invention, the separation of the hepatitis associated antigen is accomplished by a selective precipitation technique. It is known that polyethylene glycol may be used in the fractionation of complex protein mixtures, A. Polson et al, Biochim. Biophys. Acta 82 (1964) 463-475. Polyethylene gylcol has been used to concentrate hepatitis associated antigen by selective precipitation techniques, for example, Allan J. Johnson, Annals New York Academy of Sciences Vol. 240 (1975) 162-164. Also, ethylene oxide-propylene glycol condensation products have been used to selectively precipitate various blood plasma fractions without reference to the presence or absence of hepatitis associated antigen, Fekete et al. U.S. Pat. No. 3,770,631.

According to the present invention, utilization of ethylene oxide-propylene glycol condensation products in certain concentrations and at certain temperature values will result in the formation of liquid and solid phases in an aqueous admixture of plasma with the hepatitis associated antigen being isolated entirely in one of the phases. More specifically, in such an admixture when the concentration of the block copolymer is at least approximately 9 percent, on a weight per volume basis, and the temperature is at a value of from approximately 0° to 39° centigrade, with the concentration of the block copolymer being increased with increasing temperature up to a value of approximately 28 percent at 39° centigrade, all of the hepatitis associated antigen is isolated in the solid phase. If the concentration of the block copolymer is not increased with increasing temperature, two phases may be formed but each of them will contain some hepatitis associated antigen. At block copolymer concentrations of less than approximately 7 or 15 percent at 0° to 39° centigrade, respectively, all of the hepatitis associated antigen will appear in the liquid phase. When complete precipitation of the hepatitis associated antigen is desired, the upper limit on the concentration of the block copolymer is its limit of solubility at the temperatures involved.

The particular block copolymers which are utilized in the selective precipitation procedures of this invention are conveniently prepared by condensing ethylene oxide with polyoxypropylene polymer. The resultant condensation products are well known materials which can be represented by the following structural formula:

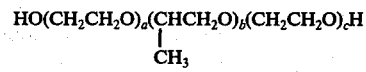

wherein $a$ and $c$ are the number of oxyethylene units and $b$ is the number of oxypropylene units. Block copolymers suitable for the purpose of this invention are available from Wyandotte Chemicals Corp. under the designations "Pluronic F-38" and "Pluronic F-68." The Pluronic F-38 material contains about 80 percent polyoxyethylene units, and the polyoxypropylene polymer portion of the molecule has a molecular weight of about 950. The condensation product has a total molecular weight of about 4,750. The Pluronic F-68 material also contains about 80 percent of polyoxyethylene units, and the polyoxypropylene polymer portion of the molecule has a molecular weight of about 1,750 with the total molecular weight of the condensation product being about 8,750. In general the block copolymers which are suitable for use in the selective precipitation procedures of this invention contain at least about 50 percent ethylene oxide units in the molecule, and the polyoxypropylene polymer portion of the molecule has a molecular weight of at least about 900. The material must be water soluble up to concentrations of at least about 20 percent on a weight per volume basis at temperatures of from about zero to 10° centigrade. The materials must be nontoxic. The block copolymer should be selected so that the lyophilized hepatitis associated antigen free product that results from the utilization of the present invention is very readily soluble. With certain plasma fractions the rate of resolubilization is very important. For example, when Factor IX is resolubilized from the lyophilized form, it begins to form thrombus very quickly. Because of the ever present risk of thrombus formation with this clotting protein, it is necessary that the material used in effecting the selective precipitation be one that does not reduce the resolubilization rate, and if possible, it should accelerate the resolubilization step. The above described block copolymers accelerate the resolubilization of the lyophilized product.

The following specific examples are submitted to illustrate and not to limit the present invention. All percentages are on a weight per volume percent basis unless otherwise indicated.

EXAMPLE I

A concentrated pooled blood plasma which was known to contain hepatitis associated antigen was anticoagulated with 3.8 weight percent sodium citrate and the pH was adjusted to 7.0 with one normal hydrochloric acid. The salt concentration of the plasma was about 0.15 molar sodium chloride. The temperature of the plasma was maintained at about 14° centigrade. About 6 percent on a weight per volume basis of a block copolymer was added to the plasma and dissolved therein. The block copolymer was an ethylene oxide-propylene glycol condensation product in which about 80 percent of the block copolymer consisted of polyoxyethylene units. The polyoxypropylene portion of the polymer had a molecular weight of about 1750. The total molecular weight of the block copolymer was about 8750. This material is available commercially from Wyandotte Chemicals Corp. under the designation "Pluronic F-68." The plasma was stirred for about 25 minutes during which period of time a precipitate formed therein. The resulting mixture was centrifuged at about 5,000 gravities for 15 minutes. The resultant hepatitis associated antigen containing supernate was decanted; the pH was checked to insure that it remained at 7.0. The precipitate contained no hepatitis associated antigen. An additional 15 percent on a weight per volume basis of the same block copolymer was added to the supernate and dissolved therein for a total concentration of 21 percent. The temperature of the supernate was adjusted to about 20° centigrade, and the mixture was stirred for about 30 minutes. During this 30 minute period of time a precipitate formed in the supernate. The mixture was then centrifuged at about 5,000 gravities for about 15 minutes, and the resultant hepatitis associated antigen free supernate was decanted. The precipitate from this second centrifuging operation was dissolved in buffered 0.15 molar saline (0.03 percent imidazole—0.0135 molar sodium citrate—saline at pH of 7.4). The final buffered saline solution had a high titer of hepatitis associated antigen.

The redissolved precipitate with its high titer of hepatitis associated antigen was used in subsequent examples as a positive control.

Substitution of a second block copolymer for the block copolymer used in this Example I results in an equally effective isolation of the hepatitis associated antigen in the second recovered precipitate. The second block copolymer is an ethylene oxide-propylene glycol condensation product which contains about 80 percent polyoxyethylene units, and the polyoxypropylene present in the copolymer has a molecular weight of about 950. The total molecular weight of the block copolymer is about 4,750. This material is commercially available from Wyandotte Chemicals Corp. under the trade designation "Pluronic F-38."

Repeating this example with concentrated pooled blood plasma, it is found that the concentration of the blood plasma should be such that the total protein concentration therein is no greater than approximately 4 percent on a weight per volume basis.

EXAMPLE II

A citrate free sample of hepatitis associated antigen containing diluted prothrombin containing blood plasma was adjusted to a pH of 7.0 with one normal hydrochloric acid. The plasma was diluted one part by volume to one part by volume of saline solution. The protein concentration in the resultant plasma was about 3.3 percent on a weight per volume basis (grams per 100 cubic centimeters) and the salt concentration was 0.15 molar sodium chloride. Fifteen percent on a weight per volume basis of the block copolymer described in Example I, and identified by the trade designation "Pluronic F-68" was dissolved in the concentrated plasma, and the mixture was continually stirred for 15 minutes at a temperature of about 20 degrees centigrade. A precipitate formed in the plasma. The resultant admixture was centrifuged at 5,000 gravities for 15 minutes. The supernate was decanted to separate it from the precipitate. The decanted supernate was free of hepatitis associated antigen. The precipitate contained hepatitis associated antigen. The supernate was suitable for further processing to recover prothrombin complex factors or any other fractions.

Repetition of this Example II utilizing 20 percent on a weight per volume basis of the lower molecular weight block copolymer described above in Example I, and having the trade designation "Pluronic F-38", results in the recovery of a hepatitis associated antigen free supernate and a precipitate which contains hepatitis associated antigen. In general, the concentrations required to effect complete separation with the lower molecular weight "Pluronic F-38" are slightly greater than, but approximately the same as those at which "Pluronic F-68" is used.

This Example II is carried out as one step in a procedure for separating prothrombin complex factors from plasma which initially contains hepatitis associated antigen. The prothrombin complex factors which are recovered from the procedure in the form of a prothrombin complex concentrate are free of hepatitis associated antigen.

The supernate recovered as in this Example II is processed further by changing the pH to 5.2 with 1 normal hydrochloric acid and a precipitate is allowed to form for 30 minutes while the admixture is stirred continually. The resultant precipitate is dissolved in citrated saline solution and is sterilized by millipore filtration.

Carrying out the procedure of this Example II as one step in the preparation of Factor IX concentrates results in the preparation of a hepatitis associated antigen free material. The supernate which is the product obtained from practicing the procedure of Example II is precipitated at a pH of 5.2 and is recovered and sterilized for use.

Repetition of this Example II utilizing Fraction III or IV starting materials likewise results in the preparation of a hepatitis associated antigen free product.

EXAMPLE III

Citrated cryoprecipitated blood plasma containing hepatitis associated antigen was thawed at from 2 to 5 degrees centigrade and the resultant liquid plasma was centrifuged at 5,000 gravities for 15 minutes. The plasma supernate was decanted from the cryoprecipitate. The resultant cryoprecipitate was extracted in 0.15 molar sodium chloride solution containing as a buffer 0.02 molar tris-saline having one-tenth of the original plasma volume, and the pH was adjusted to a value of 6.5 with one normal hydrochloric acid. In a first separation step, two percent on a weight per volume basis of a block copolymer was added to the mixture. The mixture contained about 3 percent on a weight per volume basis of total protein. The block copolymer used was that described in Example I which is identified by the trade designation "Pluronic F-68." The mixture was stirred at a temperature of about 22° centigrade for about 30 minutes, and the resultant precipitate was separated by centrifuging at 5,000 gravities for 30 minutes. The hepatitis associated antigen free fibrinogen precipitate was separated from the hepatitis associated antigen containing cryosupernate. In a second separation step, the cryosupernate was cooled to a temperature of approximately 3° centigrade; the pH was adjusted to a value of 6.88; and an additional amount of "Pluronic F-68" was dissolved in the mixture to bring the total concentration of this block copolymer to 5 percent on a weight per volume basis. The resultant admixture was stirred for 30 minutes, and the resultant precipitate was centrifuged down at 5,000 gravities for 30 minutes. The resultant precipitate contained hepatitis associated antigen free Factor VIII. The supernate containing the hepatitis associated antigen was discarded.

Repetition of this Example III utilizing concentrations of "Pluronic F-68" at 4.5 percent in the first step and 3.5 percent in successive examples in the second step likewise results in the preparation of hepatitis associated antigen free fibrinogen and Factor VIII precipitates. Various precipitation times in the first and second steps of from 15 to 30 minutes are effective in accomplishing the required precipitation. The substitution of the block copolymer described in the Example I above and identified by the trade designation "Pluronic F-38" in this example also results in the production of hepatitis associated antigen free fibrinogen and Factor VIII precipitates.

The ionic concentration of the various aqueous plasma admixtures which are utilized in practicing the present invention generally range from about 0.5 to 0.05 molar sodium chloride and preferably from about 0.20 to 0.10 molar sodium chloride. Below 0.05 molar sodium chloride it is very difficult to isolate the hepatitis associated antigen in either the liquid or the solid phase. At ionic strengths above about 0.5 molar sodium chloride the potency of the clotting factors begins to be impaired. For purposes of convenience and safety the ionic concentration is generally maintained at approximately the physiological value of 0.15 molar sodium chloride.

The temperatures at which the various procedures of the present invention may be accomplished range from approximately 0° centigrade to approximately 39 degrees centigrade. Above 39° centigrade the potency of certain of the clotting factors is very quickly destroyed and below 0° centigrade the problem of freezing is encountered with the aqueous solutions which are involved. In general, the selective precipitation procedures which are utilized are carried out at approximately 22° centigrade so that no special cooling or heating procedures are required.

In general, in order to accomplish separation and avoid impairing the potency of certain of the clotting factors the pH should be maintained at values between approximately 6.5 and 7.5. Separation of the hepatitis associated antigen is generally accomplished more easily within this range of pH values.

The procedures for removing the hepatitis associated antigen according to the present invention may conveniently be practiced as one step in an otherwise conventional concentrative or fractionating procedure.

What is claimed:

1. Process for separating hepatitis associated antigen from certain desired blood plasma fractions comprising:
    preparing an aqueous admixture including the desired blood plasma fraction and from about 2 to 7 weight per volume percent of a block copolymer of ethylene oxide and polyoxypropylene polymer at a temperature of approximately 22 degrees centigrade and a pH of from about 6.5 to 7.5 to form a precipitate in said admixture;
    separating said precipitate from said admixture; and
    retaining said precipitate for beneficial use.

2. Process of claim 1 wherein said temperature is adjusted to a value of about 20 degrees centigrade and the concentration of said block copolymer is adjusted to a value of about 2 weight per volume percent.

3. Process of claim 1 including selecting a concentrated aqueous blood plasma composition.

4. Process for removing hepatitis associated antigen from blood plasma comprising:
    selecting a quantity of said blood plasma;
    adjusting the pH of said quantity of blood plasma to a value of from about 6.5 to 7.5;
    adjusting the temperature of said quantity of blood plasma to a value of approximately 22° centigrade;
    admixing said quantity of blood plasma with from about 2 to 7 weight per volume percent of a block copolymer of ethylene oxide and polyoxypropylene polymer;
    separating the resultant liquid and solid phases; and
    recovering the resultant hepatitis associated antigen free solid phase.

* * * * *